US00PP19484P2

(12) United States Plant Patent
Zary

(10) Patent No.: US PP19,484 P2
(45) Date of Patent: Nov. 25, 2008

(54) SHRUB ROSE PLANT NAMED 'JACLOOSE'

(50) Latin Name: *Rosa hybrida*
Varietal Denomination: JACloose

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,218

(22) Filed: Nov. 28, 2007

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent L. Bell
*Assistant Examiner*—Georgia Helmer
(74) *Attorney, Agent, or Firm*—Klarquist Sparkman, LLP

(57) ABSTRACT

Shrub rose plant having excellent resistance to rust, powdery mildew and blackspot; arching, weeping habit of growth; large clusters of flowers; ease of rooting as a softwood cutting; and female sterility.

1 Drawing Sheet

Genus and species: *Rosa hybrida.*
Variety denomination: 'JACloose'.

ORIGIN OF THE INVENTION

The present invention relates to a new and distinct variety of a shrub rose plant named 'JACloose' which was originated by me by crossing an unnamed variety (unpatented, seed parent), with 'TANotax' (U.S. Plant Pat. No. 11,572, pollen parent). The seed parent is a cross, 'MACminmo' (U.S. Plant Pat. No. 7,319)×82-01752 (unpatented).

BACKGROUND OF THE INVENTION

The primary objective of this breeding was to produce a new shrub rose variety having the excellent disease resistance of both parents combined with the weeping habit of the female parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Excellent resistance to rust, powdery mildew and blackspot.
2. Arching, weeping habit of growth.
3. Large clusters of flowers.
4. Ease of rooting as a softwood cutting.
5. Female sterility.

The canes of my new variety weep easily under the weight of the blooms. This make the new variety a good "weeping" tree rose and a good rose where cascading is desired, such as for some container applications.

Asexual reproduction of this new variety by cuttings, as performed at Wasco, Calif., shows that the foregoing characteristics and distinctions come true to form and are established and transmitted through succeeding propagations.

COMPARISON WITH PARENTS

'JACloose' differs from the female parent in flower color (red for the seed parent versus pink for 'JACloose') and petal count (typically 10 for the seed parent versus typically 40–45 for 'JACloose'). 'JACloose' differs from the male parent in petal count (typically 20–25 for 'TANotax' versus typically 40–45 for 'JACloose') and plant growth habit (upright for 'TANotax' versus weeping for 'JACloose').

COMPARISON WITH SIMILAR VARIETY

The variety 'JACloose' is similar to 'MEIdomonac' (U.S. Plant Pat. No. 5,105) in habit (arching and petal count), but differs in plant size ('JACloose' is smaller when mature, typically 3'×3' while 'MEIdomonac' is 5'×4') and flower form ('JACloose' is old-fashioned in form while 'MEIdomonac' is moderate in form).

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—Unnamed variety (not patented). Parentage of seed parent is 'MACminmo' (U.S. Plant Pat. No. 7,319)×82-01752.

*Pollen parent.*—'TANotax' (U.S. Plant Pat. No. 11,572).

FLOWER

Observations made from January 2005 to October 2007 of plants three years of age at the end of the observation period that were grown in a garden environment at Somis, Calif.

Blooming habit: Continuous.

Bud:

*Size.*—About 15 mm and 15 mm in diameter when the petals start to unfurl.

*Form.*—The bud form is medium in length, pointed ovoid, broad based.

*Color.*—When sepals first divide, bud color is Red-Purple Group 63B. When half blown, the upper sides of the petals are between Red-Purple Group 63B and the lower sides of the petals are Red-Purple Group 63B.

*Sepals.*—Color: Upper surface: Green Group 138B. Lower surface: Yellow-Green Group 146B. Length: 15 mm. Width: 6 mm. Shape: Subulate. Surface: Hoary. There are three lightly appendaged sepals. There are two unappendaged sepals with hairy edges.

*Receptacle.*—Color: Yellow-Green Group 146B. Shape: Funnel. Size: Small, about 9 mm long×6 mm wide. Surface: Smooth.

*Peduncle.*—Length: Short, averaging about 34–35 mm. Surface: Smooth with a very few glands. Color: Yellow-Green Group 146B. Strength: Bending, slender.

Bloom:

*Size.*—Medium. Average open diameter is about 55–60 mm.

*Borne.*—Several together in clusters of 10–13 blooms having paniculate shape.

*Stems.*—Strength: Weak. Average length is about 30–40 cm with a diameter of 3–4 mm.

*Form.*—When first open: Cupped. Permanence: All petals curl to form a bloom that is imbricate.

*Petalage.*—Number of petals under normal conditions: 40–45. Color: The upper sides of the petals are Red-Purple Group 63B. The reverse sides of the petals are Red-Purple Group 63B. The base of the petals has a Yellow-Green Group N155D color spot, about 4 mm×4 mm. The major color on the upper sides is Red-Purple Group 63B.

*Variegations.*—None observed.

*Discoloration.*—The general tonality at the end of the first day: Little change. At the end of the third day: A general fading beginning with the outer petals but by day 5 across all the petals to Red-Purple Group 63C and at petal drop to Red-Purple Group 63D.

*Fragrance.*—Slight. Peppery.

Petals:

*Thickness.*—Thin.

*Surface texture.*—Smooth.

*Shape.*—Obdeltoid on the petals on the outside of the flower to spatulate on the inner row of petals.

*Margin.*—Entire.

*Form.*—Tips slightly recurved.

*Arrangement.*—Imbricated.

*Petaloids.*—Number: 1–7, 3–7 mm long and 1–4 mm wide. Color is like the petals. Fade in the same way. Color: See petal color.

*Persistence.*—Petals drop off cleanly before drying.

*Lastingness.*—On the plant: Fair (about 5–6 days). As a cut flower: Fair (about 6–7 days).

Reproductive parts:

*Stamens.*—Number: Few, 9–15. Length: 7–8 mm. Anthers: Length: 1 mm. Color: Yellow Group 2D. Filaments: Color: White Group 155A, Length: 6–7 mm. Pollen: None Observed. Sterile.

*Pistils.*—Number: Few. 15–20. Length: 8–9 mm. Styles: Color: Yellow-White Group 158D. Length: 7–8 mm. Stigmas: Color: Greyed-Yellow Group 161D. Length: 1 mm.

*Hips.*—None observed.

PLANT

*Form.*—Shrub.

*Growth.*—Vigorous, branching, sprawling, weeping.

*Age to maturity.*—Two years.

*Mature plant.*—Height: 3 ft. Width: 3 ft.

*Rootstock.*—Own root.

Foliage: Number of leaflets on normal mid-stem leaves: 5 or 7.

*Size.*—Medium. About 11 cm long×8 cm wide.

*Quantity.*—Abundant.

*Color.*—New foliage: Upper side: Greyed-Red Group 178B. Lower side: Greyed-Red Group 178C. Old foliage: Upper side: Green Group 139A. Lower side: Green Group 137A.

Leaflets:

*Size.*—About 35 mm long×22 mm wide.

*Shape.*—Oval.

*Base shape.*—Rounded.

*Apex shape.*—Acuminate.

*Texture.*—Smooth.

*Edge.*—Serrated.

*Serrations.*—Single, small.

*Petiole.*—Color: Yellow-Green Group 146C.

*Petiole rachis.*—Color: Yellow-Green Group 146C. Underside: Smooth with an occasional prickle.

*Auricles.*—None observed.

*Stipules.*—Length: 8–9 mm, serrated, bearded.

*Disease resistance.*—Resistant to mildew, rust and blackspot under normal growing conditions.

*Pest resistance.*—None observed.

*Vein color.*—

*Venation pattern.*—Reticulate.

Wood:

*New wood.*—Color: Yellow-Green Group 147B. Bark: Smooth.

*Old wood.*—Color: Green Group 137C. Bark: Smooth.

Prickles:

*Quantity.*—Ordinary, on main canes from base: 10–12 per 15 cm of wood. Ordinary, on laterals from main canes: 10–12 per 15 cm of wood.

*Form.*—Hooked downward.

*Length.*—4–5 mm.

*Color when young.*—Greyed-Red Group 178B.

*Color when mature.*—Greyed-Orange Group 176A.

Small prickles:

*Quantity.*—On main stalks: None. On laterals: None.

Winter hardiness: Hardy to Zone 5.

I claim:

1. A new and distinct variety of shrub rose plant, substantially as herein shown and described, characterized particularly by its excellent resistance to rust, powdery mildew and blackspot; arching, weeping habit of growth; large clusters of flowers; ease of rooting as a softwood cutting; and female sterility.

* * * * *

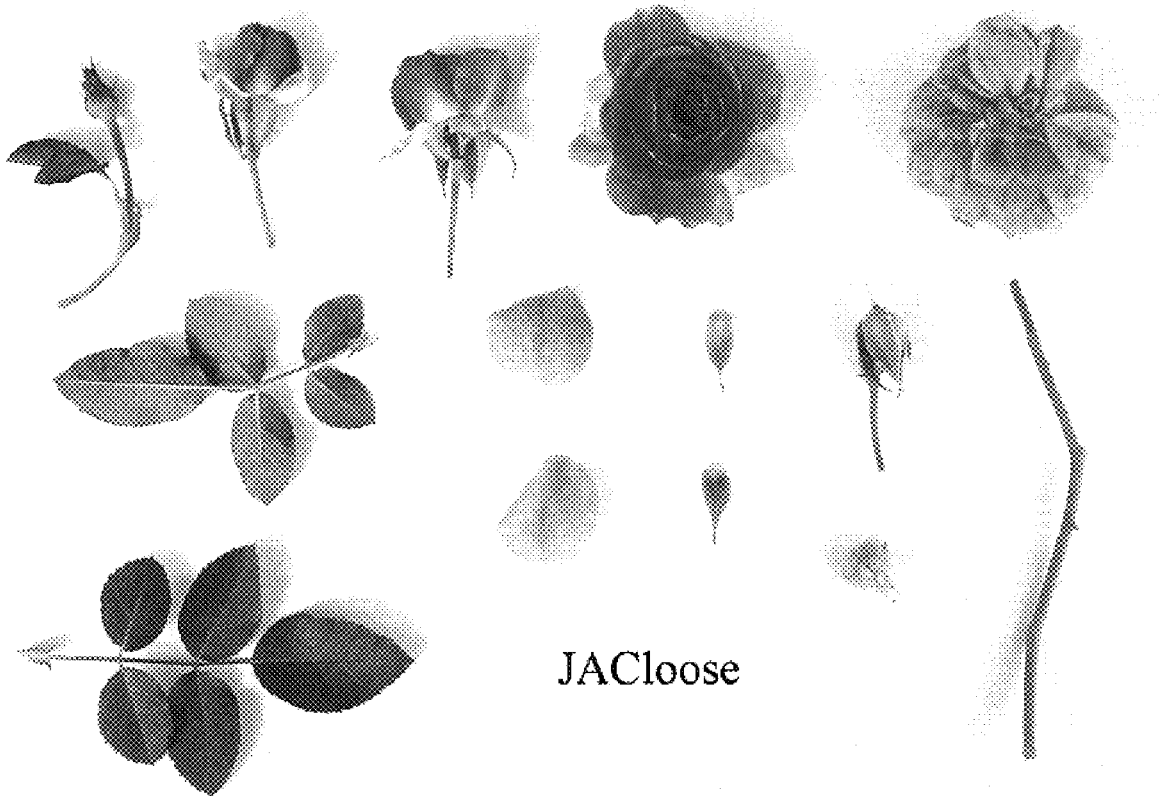
JACloose

UNITED STATES PATENT AND TRADEMARK OFFICE

CERTIFICATE OF CORRECTION

PATENT NO. : PP 19,484 P2
APPLICATION NO. : 11/998218
DATED : November 25, 2008
INVENTOR(S) : Zary It is certified that error appears in the above-identified patent and that said Letters Patent is hereby corrected as shown below:

In the Specification:

Column 2, line 18, "moderate" should read --modern--

Signed and Sealed this

Thirty-first Day of August, 2010

David J. Kappos

David J. Kappos
*Director of the United States Patent and Trademark Office*